(12) United States Patent
Pazenok et al.

(10) Patent No.: US 8,236,986 B2
(45) Date of Patent: Aug. 7, 2012

(54) PROCESS FOR PREPARING ACYLSULFAMOYLBENZAMIDES

(75) Inventors: Sergiy Pazenok, Kelkheim (DE); Mark James Ford, Bad Soden (DE); Guenter Schlegel, Liederbach (DE)

(73) Assignee: Bayer CropScience GmbH, Frankfurt (DE)

( * ) Notice: Subject to any disclaimer, the term of this patent is extended or adjusted under 35 U.S.C. 154(b) by 0 days.

(21) Appl. No.: 12/557,727

(22) Filed: Sep. 11, 2009

(65) Prior Publication Data

US 2010/0094052 A1 Apr. 15, 2010

Related U.S. Application Data

(62) Division of application No. 10/874,966, filed on Jun. 23, 2004, now Pat. No. 7,608,736.

(30) Foreign Application Priority Data

Jun. 25, 2003 (EP) .................................... 03014232

(51) Int. Cl.
C07C 303/04 (2006.01)
C07C 307/02 (2006.01)
(52) U.S. Cl. ........................................... 564/80; 564/86
(58) Field of Classification Search .................. 564/80, 564/86
See application file for complete search history.

(56) References Cited

U.S. PATENT DOCUMENTS 6,251,827 B1 6/2001 Ziemer et al. ................. 504/130

FOREIGN PATENT DOCUMENTS

WO WO 99/16744 4/1999

*Primary Examiner* — James O Wilson
*Assistant Examiner* — Ebenezer O Sackey
(74) *Attorney, Agent, or Firm* — Frommer Lawrence & Haug LLP

(57) ABSTRACT

The invention relates to a process for the preparation of a compound of formula (I):

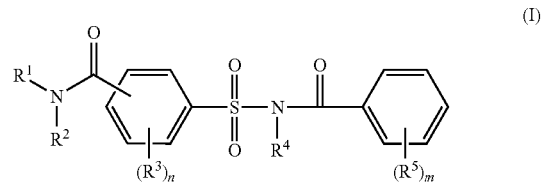

Which comprises reaction of a compound of formula (II) with a compound of the formula (III) in the presence of a chlorinating agent, followed by reaction of the resultant compound of the formula (IV) with a compound of formula (V) in the presence of a base:

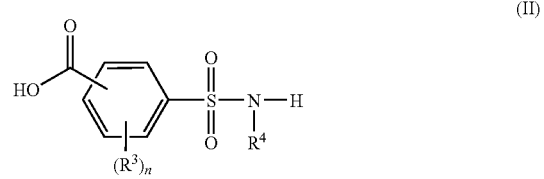

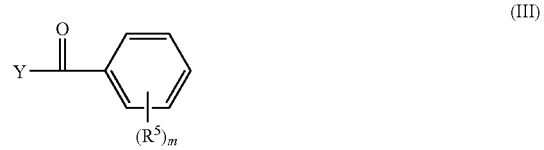

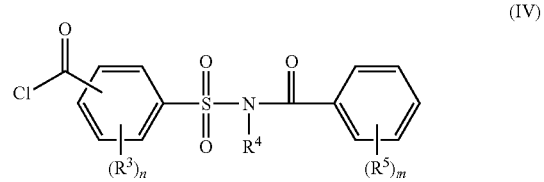

$R^1R^2NH$ (V)

wherein the various symbols are as defined in claim 1.

15 Claims, No Drawings

PROCESS FOR PREPARING ACYLSULFAMOYLBENZAMIDES

This invention relates to the technical field of chemical processes for the preparation of compounds, particularly a novel process for the preparation of a wide range of acylsulfamoylbenzamides, which compounds are useful, e.g. as safeners for pesticides.

The use of safeners is an increasingly valuable tool for extending the practical utility of many types of pesticides, in particular herbicides, in crops of useful plants such as maize, rice, or cereals, particularly in post-emergence application.

Patent Publication Number WO 99/16744 describes acylsulfamoylbenzamide derivatives and their use as safeners for the control of weeds by herbicides. The safened herbicide mixtures possess very desirable agronomic properties and may potentially of commercial utility.

Various processes are described for the preparation of these compounds in the above publication, however these methods are not always very efficient and generally require many reaction steps from readily available starting materials. Consequently it is of value to develop a new process which does not suffer from these disadvantages and can therefore be useful for industrial scale operations.

Two general processes for preparing acylsulfamoylbenzamide derivatives are described in WO 99/16744.

The first process described involves the acylation of a sulfamoylbenzamide using a benzoic acid halide, anhydride or carbonylimidazolide, or using a benzoic acid and a coupling agent such as N,N-dicyclohexylcarbodiimide. A number of specific examples of this process are described therein, which are carried out by heating a mixture of a benzoic acid with the sulfamoylbenzamide, 1,1'-carbonyldiimidazole and 1,8-diazabicyclo[5.4.0]undec-7-ene (DBU) in tetrahydrofuran. However this procedure is of limited value for large scale or industrial operations because of the moderate yields obtained, as well as the prohibitively expensive 1,1'-carbonyldiimidazole which additionally gives rise to substantial waste by-products.

The second general process described in the above reference involves the reaction of an activated acylsulfamoylbenzoic acid derivative with an amine, but this method is not specifically exemplified therein. A disadvantage of this approach is that procedures for the preparation of the activated acylsulfamoylbenzoic acid derivative, such as the acid chloride derivative, are generally inefficient since many reaction steps are involved, leading to poor or moderate overall yields.

In order to overcome the above limitations of the known processes we have now developed a new two step process for the preparation of acylsulfamoylbenzamide compounds, which involves a reduced number of reaction steps and which is applicable to industrial scale processes.

According to the present invention there is provided a process for the preparation of a compound of general formula (I):

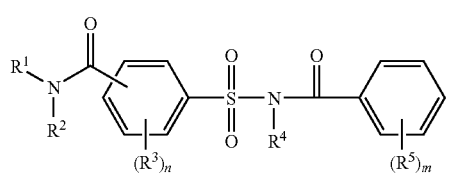

wherein:
$R^1$ is hydrogen, $-(CH_2)_p$-heterocyclyl or a hydrocarbon radical, where the two last-mentioned radicals are unsubstituted or substituted by one or more radicals selected from the group consisting of halogen, $(C_1-C_6)$-alkyl, $(C_1-C_6)$-haloalkyl, $(C_1-C_6)$-alkoxy, cyano and nitro;
$R^2$ is hydrogen, $(C_1-C_6)$-alkyl, $(C_2-C_6)$-alkenyl, $(C_2-C_6)$-alkynyl, $(C_1-C_6)$-alkoxy, $(C_2-C_6)$-alkenyloxy, where the five last-mentioned radicals are unsubstituted or substituted by one or more radicals selected from the group consisting of halogen, $(C_1-C_4)$-alkoxy and $(C_1-C_4)$-alkylthio; or
$R^1$ and $R^2$ together with the linking nitrogen atom form a 3- to 8-membered saturated or unsaturated ring;
$R^3$ and $R^5$ are each independently halogen, $(C_1-C_6)$-alkyl, $(C_1-C_6)$-haloalkyl, $(C_1-C_6)$-alkoxy, $S(O)_q$—$(C_1-C_6)$-alkyl, $(C_1-C_6)$-alkylcarbonyl, —CO-aryl, cyano or nitro; or two adjacent $R^5$ groups form a —O—$CH_2CH_2$— moiety;
$R^4$ is hydrogen, $(C_1-C_4)$-alkyl, $(C_2-C_4)$-alkenyl or $(C_2-C_4)$-alkynyl;
n is an integer from 0 to 4;
m is an integer from 0 to 5;
p is 0 or 1; and
q is 0, 1 or 2; or a salt thereof; which process comprises:
a) the reaction of a compound of general formula (II):

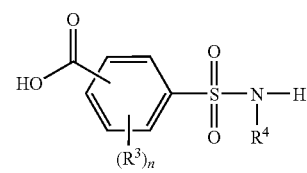

wherein $R^3$, $R^4$ and n are as defined in formula (I), with a compound of formula (III):

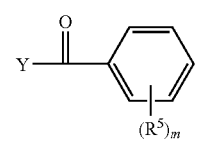

wherein $R^5$ and m are as defined in formula (I) and Y is OH or Cl, in the presence of a chlorinating agent, to give a compound of formula (IV):

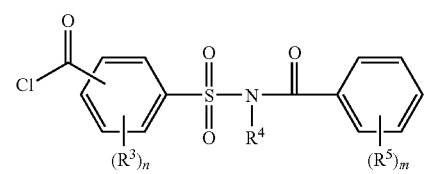

wherein $R^3$, $R^4$, $R^5$, m and n are as defined in formula (I), and
b) the reaction of the compound of formula (IV) obtained in step a) with a compound of formula (V):

$R^1R^2NH$ 

wherein $R^1$ and $R^2$ are as defined in formula (I).

The chlorinating agent used in the process is preferably selected from a sulfur or phosphorous based chlorinating agent such as thionyl chloride, phosphorus oxychloride or phosphorus pentachloride, and a carbon based chlorinating agent used for converting a carboxylic acid into the corresponding acid chloride, such as oxalyl chloride or phosgene. The preferred chlorinating agent is thionyl chloride.

The amount of chlorinating agent used has an influence on the yield of product of formula (IV) and can be optimised by way of preliminary testing depending on the solvent, the amount and type of starting material amongst other factors. In most cases the amount is between slightly below the stoichiometric amount up to an excess.

The amount of chlorinating agent used depends upon the definition of Y in formula (III), for example when Y is OH compounds of formula (IIIa):

(IIIa)

are used as starting material. Alternatively when Y is Cl compounds of formula (IIIb):

(IIIb)

are used.

When Y is OH, the amount of chlorinating agent used is preferably from 1 to 2 molar equivalents per equivalent of carboxylic groups of compounds (II) and (IIIa), more preferably from 1.1 to 2 molar equivalents per equivalents of (II) and (III), most preferably from 1.2 to 1.9 molar equivalents per equivalents of (II) and (III). When Y is Cl, the amount of chlorinating agent used is preferably from 1 to 2 molar equivalents per equivalent of compound (II), more preferably from 1.1 to 2 molar equivalents per equivalent of (II), most preferably from 1.2 to 1.9 molar equivalents per equivalent of (II).

In reaction step a) the compound of formula (IV) can be isolated by common or customary methods, for instance preferably by partial evaporation during which it precipitates and may be filtered off.

In a further feature of the invention the unreacted excess chlorinating agent, which in the case of thionyl chloride is present in the distillate, may be recycled.

The ratio of (II):(IIIa) is preferably 1:1, but in some cases it is beneficial to add a slight excess (up to 10%) of the acid (IIIa), which has the advantage of ensuring a more complete conversion of the acid (II) in the reaction. This variation is preferably used if the corresponding acid chloride of formula (IIIb) remains soluble in the reaction mixture after partial evaporation, since separation from the precipitated desired product (IV) is then effected.

A catalyst such as a N,N-dialkylacylamide, for example N,N-dimethylformamide or N,N-dibutylformamide, or a cyclic amine such as pyridine or quinoline is optionally also present in the reaction mixture.

The reaction can be conducted in the absence or preferably presence of a stable and inert solvent, which can be an non-polar or a polar organic solvent which essentially do not react with the chlorinating agent or the compounds (III) or (IV) in the reaction mixture. It is for example a non-polar organic solvent which is preferably selected from aliphatic or aromatic hydrocarbons such as alkanes, for example heptane, octane, or an alkylated benzene such as toluene, dimethylbenzenes (xylols) or trimethylbenzenes, or paraffin oil, halogenated aliphatic hydrocarbons such as dichloromethane, or halogenated aromatic hydrocarbons such as chlorobenzene or dichlorobenzene, or haloalkylbenzenes such as benzotrifluoride, and silicon oils.

The most preferred solvents are chlorobenzene and toluene.

The reaction temperature in step a) may vary within wide limits dependent on the solvent and pressure used. For example, the reaction temperature is from 70° C. to 140° C., preferably from 80° C. to 130° C., more preferably from 80° C. to 115° C.

The reaction step a) generally proceeds in excellent yield, with typical yields of the compound of formula (IV) in excess of 90% or even 95%. The purity of the compound of formula (IV) is generally very high (typically at least 95%).

The acid chloride derivative of formula (IIIb) above is formed as an intermediate in the preferred reaction where the compound of formula (IIIa) is used as starting material, and acylates the sulfamoyl moiety of the compound of formula (II) and/or its acid chloride derivative of formula (VI):

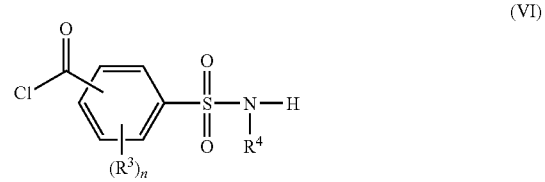

(VI)

In contrast with the above-mentioned preparation of acylsulfamoyl benzoic acid chlorides from the corresponding benzoic acids of formula (III) via separate chlorination of the compound of formula (II), unwanted dimeric side-products are essentially avoided in the process of the invention.

The reaction of the compound of formula (IV) with the compound of formula (V) in step b) can be performed with or without an additional base. Preferably an additional base is used in which case it may be an inorganic base such as an alkali metal hydroxide or alkoxide, for example sodium hydroxide, potassium hydroxide or sodium methoxide, or an alkali metal carbonate such as potassium carbonate, sodium carbonate or lithium carbonate, or an alkali metal bicarbonate such as sodium bicarbonate or potassium bicarbonate, or an alkali metal alkanoate such as sodium acetate, or an alkaline earth metal hydroxide, carbonate or bicarbonate, or an organic base such as a trialkylamine for example triethylamine or tributylamine, or a N-dialkylaniline such as dimethylaniline.

The preferred additional base is triethylamine, potassium carbonate or sodium carbonate.

The amount of the additional base used can generally be varied within wide limits and optimized by preliminary testing. Preferably the ratio of molar equivalents of additional base to molar equivalents of the compound of formula (IV) is from 1.2:1 to 1:1.2, more preferably equimolar amounts of base and compound (IV).

The amount of amine (V) used is preferably a small excess in relation to the amount of (IV), typically about 1.05 molar equivalents of (V) for 1 molar equivalent of (IV). It is also possible to use 2 molar equivalents of the compound of formula (V) wherein one molar equivalent is utilised as the base in the reaction.

The process step b) is typically carried out in the presence or absence of a solvent.

When a solvent is used a wide variety of polar or non-polar solvents may be employed, as long as they do not substantially react with the compound of formula (IV). A number of solvents may be used, for example aromatic hydrocarbons such as an alkylated benzene, for example toluene, or nitriles such as cyanoalkanes for example acetonitrile, or halogenated hydrocarbons such as haloalkanes, for example dichloromethane, or halogenated aromatic compounds such as halobenzenes, for example chlorobenzene, or ethers such as dialkyl ethers, for example diethyl ether or diglyme, or cyclic ethers such as tetrahydrofuran or dioxan, or a N,N-dialkylacylamide such as N,N-dimethylformamide or N,N-dimethylacetamide, or a N-alkylpyrrolidinone such as N-methylpyrrolidinone. Nitrile solvents are preferred, most particularly acetonitrile.

The reaction temperature for step b) is preferably from 0° C. to 150° C., more preferably from 0° C. to 60° C., most preferably from 10° C. to 20° C.

The product of formula (I) can be isolated in a simple manner, for example by dilution of the reaction mixture with water, followed by acidification with, for example a mineral acid such as hydrochloric acid, and filtration.

The isolated yield of the compound of formula (I) is generally very high, typically in excess of 90% or even 95%. The product is generally obtained in high purity, typically at least 95%.

The process of the invention, depending upon the chlorinating agent may also be carried out as a one-pot procedure. In this variation, reaction step a) is preferably followed by removal (for example by evaporation) of remaining chlorinating agent, followed in the same pot by the reaction step b).

In a further feature of the invention there is provided a process for the preparation of a compound of formula (IV) as defined above, by the reaction of a compound of formula (II) as defined above, with a compound of formula (III), preferably compound (IIIa) as defined above, in the presence of a chlorinating agent as defined above (preferably thionyl chloride).

In a further feature of the invention there is provided a process for the preparation of a compound of formula (IV) as defined above, by the reaction of a compound of formula (II) as defined above, with a compound of formula (IIIb) as defined above in the presence of a chlorinating agent as defined above (preferably thionyl chloride).

In a further feature of the invention there is provided a process for the preparation of a compound of formula (I) as defined above, by the reaction of a compound of formula (IV) as defined above, with a compound of formula (V) as defined above:

In the formula (I) and all the formulae hereinabove and hereinbelow, the terms mentioned have the meanings outlined below:

The term "halogen" includes fluorine, chlorine, bromine and iodine.

The term "$(C_1-C_4)$-alkyl" is to be understood as a straight-chain or branched hydrocarbon radical having 1, 2, 3 or 4 carbon atoms, for example the methyl, ethyl, propyl, isopropyl, 1-butyl, 2-butyl, 2-methylpropyl or tert-butyl radical.

Correspondingly, alkyl radicals having a greater range of carbon atoms are to be understood as straight-chain or branched saturated hydrocarbon radicals which contain a number of carbon atoms which corresponds to this range. The term "$(C_1-C_6)$-alkyl" thus includes the abovementioned alkyl radicals, and also, for example, the pentyl, 2-methylbutyl, 1,1-dimethylpropyl and hexyl radical.

"$(C_1-C_4)$-haloalkyl" or "$(C_1-C_6)$-haloalkyl" are to be understood as an alkyl group mentioned under the term "$(C_1-C_4)$-alkyl" or "$(C_1-C_6)$-alkyl" respectively in which one or more hydrogen atoms are replaced by the corresponding number of identical or different halogen atoms, preferably chlorine or fluorine, such as the trifluoromethyl, the 1-fluoroethyl, the 2,2,2-trifluoroethyl, the chloromethyl, fluoromethyl, the difluoromethyl and the 1,1,2,2-tetrafluoroethyl group.

"$(C_1-C_4)$-alkoxy" or "$(C_1-C_6)$-alkoxy" are to be understood as an alkoxy group whose hydrocarbon radical has the meaning given under the term "$(C_1-C_4)$-alkyl" or "$(C_1-C_6)$-alkyl" respectively. Alkoxy groups embracing a larger range of carbon atoms are to be understood likewise.

The terms "alkenyl" and "alkynyl" having a prefix stating a range of carbon atoms denote a straight-chain or branched hydrocarbon radical having a number of carbon atoms corresponding to this range, this hydrocarbon radical having at least one multiple bond which can be in any position of the unsaturated radical in question. "$(C_2-C_6)$-alkenyl" thus denotes, for example, the vinyl, allyl, 2-methyl-2-propenyl, 2-butenyl, pentenyl, 2-methylpentenyl or the hexenyl group. "$(C_2-C_6)$-alkynyl" denotes, for example, the ethinyl, propargyl, 2-methyl-2-propynyl, 2-butynyl, 2-pentynyl and the 2-hexynyl group.

"$(C_3-C_8)$-cycloalkyl" denotes monocyclic alkyl radicals, such as the cyclopropyl, cyclobutyl, cyclopentyl, cyclohexyl, cycloheptyl or cyclooctyl radical and bicyclic alkyl radicals, such as the norbornyl radical.

"$(C_3-C_8)$-cycloalkoxy" or "$(C_3-C_8)$-cycloalkylthio" is to be understood as one of the abovementioned $(C_3-C_8)$-cycloalkyl radicals which is attached via an oxygen or sulfur atom.

"$(C_1-C_4)$-alkylthio" or "$(C_1-C_8)$-alkylthio" respectively are an alkylthio group whose hydrocarbon radical has the meaning given under the term "$(C_1-C_4)$-alkyl" or "$(C_1-C_6)$-alkyl".

Other composite terms, such as $(C_3-C_6)$-cycloalkenyl are to be understood correspondingly, in accordance with the above definitions.

The term "aryl" is to be understood as an isocyclic, mono-, bi- or polycyclic aromatic radical preferably having 6 to 14, in particular 6 to 12, carbon atoms, such as phenyl, naphthyl or biphenylyl, preferably phenyl.

The term "heterocyclyl" denotes a mono- or bicyclic radical which is fully saturated, partially or fully unsaturated and which contains one to five identical or different atoms selected from the group consisting of nitrogen, sulfur and oxygen, where, however, two oxygen atoms may not be directly adjacent and at least one carbon atom must be present in the ring, for example a thienyl, furyl, pyrrolyl, thiazolyl, oxazolyl, imidazolyl, isothiazolyl, isoxazolyl, pyrazolyl, 1,3,4-oxadiazolyl, 1,3,4-thiadiazolyl, 1,3,4-triazolyl, 1,2,4-oxadiazolyl, 1,2,4-thiadiazolyl, 1,2,4-triazolyl, 1,2,3-triazolyl, 1,2,3,4-tetrazolyl, benzo[b]thienyl, benzo[b]furyl, indolyl, benzo[c]thienyl, benzo[c]furyl, isoindolyl, benzoxazolyl, benzothiazolyl, benzimidazolyl, benzisoxazolyl, benzisothiazolyl, benzopyrazolyl, benzothiadiazolyl, benzotriazolyl, dibenzofuryl, dibenzothienyl, carbazolyl, pyridyl, pyrazinyl, pyrimidinyl, pyridazinyl, 1,3,5-triazinyl, 1,2,4-triazinyl, 1,2,4,5-tetrazinyl, quinolinyl, isoquinolinyl, quinoxalinyl, quinazolinyl, 1,8-naphthyridinyl, 1,5-naphthyridinyl, 1,6-naphthyridinyl, 1,7-naphthyridinyl, phthalazinyl, pyridopyrimidinyl, purinyl, pteridinyl, piperidinyl, pyrrolidinyl, oxazolinyl, tetrahydrofuryl, tetrahydropyranyl, isoxazolidinyl or thiazolidinyl radical.

A "hydrocarbon radical" is a straight-chain, branched or cyclic hydrocarbon radical which may be saturated, partially saturated, unsaturated or aromatic, for example alkyl, alkenyl, alkynyl, cycloalkyl, cycloalkenyl, cycloalkylalkyl, aryl or $CH_2$aryl, preferably alkyl, alkenyl and alkynyl having up to 20 carbon atoms or cycloalkyl having 3 to 6 ring atoms or phenyl.

In the cases where two or more radicals $R^3$ and/or $R^5$ are present, i.e. if m and/or n are greater than one, these radicals may in each case be identical or different.

If $R^1$ in the formula (I) is a hydrocarbon radical, this hydrocarbon radical has preferably up to 20 carbon atoms. If this hydrocarbon radical carries further carbon-containing substituents, the total number of all carbon atoms of this radical $R^1$ is preferably 2 to 30.

Depending on the kind and the linkage of the substituents, the compounds of formula (I) may be present as stereoisomers. If, for example, one or more alkenyl groups are present, diastereomers may occur. If, for example, one or more asymmetric carbon atoms are present, enantiomers and diastereomers may occur. Stereoisomers can be obtained from the mixtures which are obtained in the preparation by customary separation methods, for example by chromatographic separation processes. It is also possible to prepare stereoisomers selectively by employing stereoselective reactions using optically active starting materials and/or auxiliaries. The process thus also relates to all stereoisomers and mixtures thereof which are embraced by the formula (I) but not specifically defined.

The compounds of the formula (I) can form salts. Salt formation may occur by action of a base on those compounds of the formula (I) which carry an acidic hydrogen atom, for example in the case of $R^4$=H. Suitable bases are, for example, organic amines and also ammonium, alkali metal or alkaline earth metal hydroxides, carbonates and bicarbonates, in particular sodium hydroxide and potassium hydroxide, sodium carbonate and potassium carbonate and sodium bicarbonate and potassium bicarbonate. Salt formation can also occur by addition of an acid to basic groups, where a heterocyclyl group is present and represents a basic group such as imidazolyl or pyridyl. Acids which are suitable for this purpose are inorganic and organic acids, for example HCl, HBr, $H_2SO_4$, $HNO_3$ or $H_3PO_4$, or acetic acid, trifluoroacetic acid or oxalic acid, or sulfonic acids, and the process of the invention includes the formation of such salts.

Preferably $R^1$ is hydrogen, $(C_1-C_{12})$-alkyl, $(C_2-C_8)$-alkenyl, $(C_2-C_8)$-alkynyl, $(C_3-C_8)$-cycloalkyl, $(C_3-C_8)$-cycloalkenyl, aryl, —$CH_2$-aryl or —$(CH_2)_p$-heterocyclyl where heterocyclyl is a 3- to 8-membered ring having up to three identical or different hetero atoms selected from the group consisting of nitrogen, oxygen and sulfur, where the eight last-mentioned radicals are unsubstituted or substituted by one or more radicals selected from the group consisting of halogen, $(C_1-C_6)$-alkyl, $(C_1-C_6)$-haloalkyl, $(C_1-C_6)$-alkoxy, cyano and nitro.

Preferably also $R^1$ is hydrogen, $(C_1-C_8)$-alkyl, $(C_2-C_6)$-alkenyl, $(C_2-C_6)$-alkynyl, $(C_3-C_6)$-cycloalkyl, $(C_5-C_6)$-cycloalkenyl, phenyl or —$(CH_2)_p$-heterocyclyl where heterocyclyl is a 3- to 6-membered ring having up to three hetero atoms selected from the group consisting of nitrogen, oxygen and sulfur, where the seven last-mentioned radicals are unsubstituted or substituted by one or more substituents selected from the group consisting of halogen, $(C_1-C_6)$-alkyl, $(C_1-C_6)$-haloalkyl and $(C_1-C_6)$-alkoxy.

Preferably also $R^1$ is hydrogen, $(C_1-C_6)$-alkyl, $(C_2-C_6)$-alkenyl, $(C_2-C_6)$-alkynyl, $(C_1-C_6)$-alkoxy-$(C_1-C_6)$-alkyl, $(C_3-C_6)$-cycloalkyl, $(C_3-C_6)$-cycloalkyl-$(C_1-C_6)$-alkyl, —$CH_2$furyl, phenyl, —$CH_2$phenyl or —$CH_2CH_2$phenyl, which last three mentioned phenyl radicals are unsubstituted or substituted by one or more halogen radicals.

Preferably also $R^1$ is hydrogen, $(C_1-C_6)$-alkyl, $(C_2-C_6)$-alkenyl, $(C_3-C_6)$-cycloalkyl, $(C_5-C_6)$-cycloalkenyl, phenyl or 3- to 6-membered heterocyclyl having up to three hetero atoms selected from the group consisting of nitrogen, oxygen and sulfur, where the six last-mentioned radicals are unsubstituted or substituted by one or more substituents selected from the group consisting of halogen, $(C_1-C_4)$-alkyl, $(C_1-C_4)$-haloalkyl and $(C_1-C_4)$-alkoxy.

Preferably $R^2$ is hydrogen, $(C_1-C_6)$-alkyl or $(C_1-C_6)$-alkoxy where the two last-mentioned radicals are unsubstituted or substituted by one or more radicals selected from the group consisting of halogen and $(C_1-C_4)$-alkoxy.

Preferably also $R^2$ is hydrogen or $(C_1-C_6)$-alkyl or $(C_1-C_6)$-haloalkyl.

Preferably also $R^2$ is hydrogen, $(C_1-C_6)$-alkyl or $(C_2-C_6)$-alkynyl.

Preferably also $R^1$ and $R^2$ together form a —$(CH_2)_2$—O—$(CH_2)_2$—, —$(CH_2)_4$— or —$(CH_2)_5$— moiety.

Preferably $R^3$ and $R^5$ are each independently halogen, $(C_1-C_6)$-alkyl, $(C_1-C_6)$-haloalkyl, $(C_1-C_6)$-alkoxy, $S(O)_q$—$(C_1-C_6)$-alkyl, cyano or nitro, or $R^5$ is —CO-aryl, or two adjacent $R^5$ groups form a —O—$CH_2CH_2$— moiety.

Preferably also $R^3$ and $R^5$ are each independently halogen, $(C_1-C_4)$-alkyl, $(C_1-C_4)$-haloalkyl, $(C_1-C_4)$-alkoxy, $S(O)_q$—$(C_1-C_4)$-alkyl, cyano or nitro, or $R^5$ is —CO-aryl, or two adjacent $R^5$ groups form a —O—$CH_2CH_2$— moiety.

Preferably also $R^3$ and $R^5$ are each independently halogen, $(C_1-C_4)$-alkyl, $(C_1-C_4)$-haloalkyl, $(C_1-C_4)$-alkoxy, cyano or nitro, or $R^5$ is —CO-aryl, or two adjacent $R^5$ groups form a —O—$CH_2CH_2$— moiety.

Preferably, each $R^3$ is independently halogen, $(C_1-C_4)$-alkyl, $(C_1-C_4)$-haloalkyl, $(C_1-C_4)$-alkoxy, $S(O)_q$—$(C_1-C_4)$-alkyl, cyano or nitro.

More preferably, each $R^3$ independently is halogen, $(C_1-C_4)$-alkyl, $(C_1-C_4)$-haloalkyl, $(C_1-C_4)$-alkoxy, cyano or nitro.

More preferably, $R^3$ is halogen or nitro.

Preferably $R^4$ is hydrogen or $(C_1-C_6)$-alkyl.

More preferably $R^4$ is hydrogen or $(C_1-C_4)$-alkyl.

Most preferably $R^4$ is hydrogen.

Preferably, each $R^5$ is independently halogen, $(C_1-C_6)$-alkyl, $(C_1-C_6)$-haloalkyl, $(C_1-C_6)$-alkoxy, $S(O)_q$—$(C_1-C_6)$-alkyl, cyano, nitro, —CO-aryl, or two adjacent $R^5$ groups form a —O—$CH_2CH_2$— moiety, more preferably is halogen, $(C_1-C_6)$-alkyl, $(C_1-C_6)$-alkoxy, nitro or —CO-naphthyl, or two adjacent $R^5$ groups form a —O—$CH_2CH_2$— moiety.

More preferably, each $R^5$ is independently halogen, $(C_1-C_4)$-alkyl, $(C_1-C_4)$-haloalkyl, $(C_1-C_4)$-alkoxy, $S(O)_q$—$(C_1-C_4)$-alkyl, cyano, nitro or —CO-aryl, or two adjacent $R^5$ groups form a —O—$CH_2CH_2$— moiety, more preferably is halogen, $(C_1-C_4)$-alkyl, $(C_1-C_4)$-alkoxy, nitro or —CO-naphthyl, or two adjacent $R^5$ groups form a —O—$CH_2CH_2$— moiety.

Preferably also $R^5$ is each independently halogen, $(C_1-C_4)$-alkyl, $(C_1-C_4)$-haloalkyl, $(C_1-C_4)$-alkoxy, cyano or nitro, more preferably halogen, $(C_1-C_4)$-alkyl, $(C_1-C_4)$-alkoxy, cyano or nitro, more preferably $(C_1-C_4)$-alkoxy.

Preferably n is 0, 1 or 2, more preferably 0.

Preferably m is 0, 1 or 2, more preferably 1 or 2, in particular 1.

Preferred compounds of formula (I) are those in which:

$R^1$ is hydrogen, $(C_1-C_{12})$-alkyl, $(C_2-C_8)$-alkenyl, $(C_2-C_8)$-alkynyl, $(C_3-C_8)$-cycloalkyl, $(C_3-C_8)$-cycloalkenyl, aryl, —$CH_2$aryl or —$(CH_2)_p$-heterocyclyl where heterocyclyl is a 3- to 8-membered ring having up to three identical or different hetero atoms selected from the group consisting of nitrogen, oxygen and sulfur, where the eight last-mentioned radicals are unsubstituted or substituted by one or more radicals selected from the group consisting of halogen, $(C_1-C_6)$-alkyl, $(C_1-C_6)$-haloalkyl, $(C_1-C_6)$-alkoxy, cyano and nitro;

$R^2$ is hydrogen, $(C_1-C_6)$-alkyl or $(C_1-C_6)$-alkoxy where the two last-mentioned radicals are unsubstituted or substituted by one or more radicals selected from the group consisting of halogen and $(C_1-C_4)$-alkoxy;

$R^3$ and $R^5$ are each independently halogen, $(C_1-C_6)$-alkyl, $(C_1-C_6)$-haloalkyl, $(C_1-C_6)$-alkoxy, $S(O)_q$—$(C_1-C_6)$-alkyl, cyano or nitro, or $R^5$ is —CO-aryl, or two adjacent $R^5$ groups form a —O—$CH_2CH_2$— moiety; and $R^4$ is hydrogen or $(C_1-C_6)$-alkyl.

Further preferred compounds of formula (I) are those in which:

$R^1$ is hydrogen, $(C_1-C_8)$-alkyl, $(C_2-C_6)$-alkenyl, $(C_2-C_6)$-alkynyl, $(C_3-C_6)$-cycloalkyl, $(C_5-C_6)$-cycloalkenyl, phenyl or —$(CH_2)_p$-heterocyclyl where heterocyclyl is a 3- to 6-membered ring having up to three hetero atoms selected from the group consisting of nitrogen, oxygen and sulfur, where the seven last-mentioned radicals are unsubstituted or substituted by one or more substituents selected from the group consisting of halogen, $(C_1-C_6)$-alkyl, $(C_1-C_6)$-haloalkyl and $(C_1-C_6)$-alkoxy;

$R^2$ is hydrogen or $(C_1-C_6)$-alkyl or $(C_1-C_6)$-haloalkyl;

$R^3$ and $R^5$ are each independently halogen, $(C_1-C_4)$-alkyl, $(C_1-C_4)$-haloalkyl, $(C_1-C_4)$-alkoxy, $S(O)_q$—$(C_1-C_4)$-alkyl, cyano or nitro, or $R^5$ is —CO-aryl, or two adjacent $R^5$ groups form a —O—$CH_2CH_2$— moiety; and $R^4$ is hydrogen or $(C_1-C_4)$-alkyl.

Also preferred are compounds of formula (I) in which:

$R^1$ is hydrogen, $(C_1-C_6)$-alkyl, $(C_2-C_6)$-alkenyl, $(C_2-C_6)$-alkynyl, $(C_1-C_6)$-alkoxy-$(C_1-C_6)$-alkyl, $(C_3-C_6)$-cycloalkyl, $(C_3-C_6)$-cycloalkyl-$(C_1-C_6)$-alkyl, —$CH_2$furyl, phenyl, —$CH_2$phenyl or —$CH_2CH_2$phenyl, which last three mentioned phenyl radicals are unsubstituted or substituted by one or more halogen radicals;

$R^2$ is hydrogen, $(C_1-C_6)$-alkyl or $(C_2-C_6)$-alkynyl;

or $R^1$ and $R^2$ together form a —$(CH_2)_2$—O—$(CH_2)_2$—, —$(CH_2)_4$— or —$(CH_2)_5$— moiety;

$R^3$ is halogen or nitro;

$R^4$ is hydrogen or $(C_1-C_4)$-alkyl;

$R^5$ is halogen, $(C_1-C_6)$-alkyl, $(C_1-C_6)$-haloalkyl, $(C_1-C_6)$-alkoxy, $S(O)_q$—$(C_1-C_6)$-alkyl, cyano, nitro, —CO-aryl, or two adjacent $R^5$ groups form a —O—$CH_2CH_2$— moiety, more preferably is halogen, $(C_1-C_6)$-alkyl, $(C_1-C_6)$-alkoxy, nitro or —CO-naphthyl, or two adjacent $R^5$ groups form a —O—$CH_2CH_2$— moiety;

n is 0, 1 or 2; and m is 0, 1 or 2, more preferably 1 or 2.

Further preferred compounds of formula (I) are those in which:

$R^1$ is hydrogen, $(C_1-C_6)$-alkyl, $(C_2-C_6)$-alkenyl, $(C_3-C_6)$-cycloalkyl, $(C_5-C_6)$-cycloalkenyl, phenyl or 3- to 6-membered heterocyclyl having up to three hetero atoms selected from the group consisting of nitrogen, oxygen and sulfur, where the six last-mentioned radicals are unsubstituted or substituted by one or more substituents selected from the group consisting of halogen, $(C_1-C_4)$-alkyl, $(C_1-C_4)$-haloalkyl and $(C_1-C_4)$-alkoxy;

$R^2$ is hydrogen, $(C_1-C_6)$-alkyl or $(C_1-C_6)$-haloalkyl;

$R^3$ and $R^5$ are each independently halogen, $(C_1-C_4)$-alkyl, $(C_1-C_4)$-haloalkyl, $(C_1-C_4)$-alkoxy, cyano or nitro;

$R^4$ is hydrogen;

n is 0, 1 or 2; and m is 0, 1 or 2, more preferably 1 or 2.

Particularly preferred compounds of formula (I) are those in which:

$R^1$ is hydrogen, $(C_1-C_6)$-alkyl or $(C_3-C_6)$-cycloalkyl;

$R^2$ and $R^4$ are each hydrogen;

$R^5$ is $(C_1-C_6)$-alkoxy;

n is 0;

m is 0 or 1; more preferably 1.

and the sulfamoyl group is located para to the $CONR^1R^2$ moiety in the phenyl ring.

Also preferred are processes for the preparation of formulae (Ia), (Ib), (Ic), (IVa), (IVb) and (IVc) as shown and defined in Tables 1 to 6 below, wherein the radicals $R^1$, $R^2$, $R^3$, $R^4$, $R^5$ and n are as defined above, and preferably the preferred meanings above.

Compounds of formula (IV) are novel and form a further feature of the invention. Compounds of formula (II), (III), (V) and (VI) are known or may be prepared by known methods.

Compared with the known process, the present invention provides an overall process for the preparation of acylsulfamoylbenzamides which has fewer reaction steps, and gives higher yields and higher purity product.

The following non-limiting examples illustrate the invention.

The amounts, relative amounts, percentages or ratios refer to the weight unless another definition is specifically given.

EXAMPLE 1

4-[[(2-Methoxy-5-chlorobenzoyl)amino]sulfonyl]benzoyl chloride

A mixture of 4-aminosulfonylbenzoic acid (1 mol), 2-methoxy-5-chlorobenzoic acid (1 mol) and thionyl chloride (2.5 mol) in chlorobenzene (700 ml) was heated at 120° C. for 7-9 hours. After the reaction was complete 200 ml of the solvent was removed in vacuo. The mixture was cooled and the precipitate filtered off and washed with heptane to give the title compound, mp. 138-140° C., yield 93% of theory. 4-[[(Benzoyl)amino]sulfonyl]benzoyl chloride was prepared in a similar manner from 4-aminosulfonylbenzoic acid and benzoic acid, mp. 180-182° C., yield 96% of theory. 4-[[(2-Chlorobenzoyl)amino]sulfonyl]benzoyl chloride was prepared in a similar manner from 4-aminosulfonylbenzoic acid and 2-chlorobenzoic acid, mp. 198-200° C., yield 95% of theory.

EXAMPLE 2

N,N-Diethyl-4-[[(2-methoxybenzoyl)amino]sulfonyl]benzamide

To a suspension of 4-[[(2-methoxybenzoyl)amino]sulfonyl)benzoyl chloride (1 mol) and diethylamine (1 mol) in acetonitrile (1000 ml), was added triethylamine (1 mol) at 10° C. The mixture was stirred for 2 hours at 20° C. and diluted with water (500 ml). The white precipitate was filtered off, washed and dried to give the title compound. The yield of product obtained was 98% of theory, and the purity 98%.

EXAMPLE 3

N-Cyclopropyl-4-[[(2-chlorobenzoyl)amino]sulfonyl]benzamide

By employing the procedure described in Example 2 but using potassium carbonate (1 equivalent) instead of triethylamine, there was obtained the title compound in a yield of 99% of theory.

In the Tables 1 to 3 below are listed a number of examples of compounds of formula (I) which are prepared by the process of the invention.

The abbreviations in the tables 1 to 6 denote:

Bu=n-butyl Et=ethyl
Me=methyl c=cyclo
Pr=n-propyl s=secondary
i=iso Mp=melting point
t=tertiary If an alkyl radical is listed in the tables without any further specification, this alkyl radical is straight-chain.

TABLE 1

Compounds of formula (Ia)

(Ia)

| Cpd No. | $R^1$ | $R^2$ | $R^3$ | $R^4$ | $R^5$ | Yield % | Mp °C. |
|---|---|---|---|---|---|---|---|
| 1-1 | Et | Et | — | H | 2-OMe | 94-98 | |
| 1-2 | Bu | H | — | H | 2-OMe, 5-Me | 92-96 | 196 |
| 1-3 | Bu | H | — | H | 2-NO$_2$, 4-Cl | 86-90 | |
| 1-4 | Bu | H | — | H | 2,5-(Me)$_2$ | 83-87 | |
| 1-5 | Bu | H | — | H | 2,3-(Me)$_2$ | 86-90 | |
| 1-6 | Bu | H | — | H | 2-NO$_2$, 4-Cl | 76-80 | |
| 1-7 | Bu | H | — | Me | 2-OMe | 85-89 | |
| 1-8 | Bu | H | — | Me | 2-OMe, 5-Me | 81-85 | |
| 1-9 | Bu | H | — | Me | 2-Cl | 86-90 | |
| 1-10 | Et | Et | — | Me | 2-OMe, 5-Cl | 93-97 | |
| 1-11 | Bu | H | 2-NO$_2$ | H | 2-OMe | 93-97 | |
| 1-12 | Bu | H | 2-NO$_2$ | H | 2-OMe, 5-Me | | |
| 1-13 | Bu | H | 2-NO$_2$ | H | 2-Cl | 93-97 | |
| 1-14 | Bu | H | 2-NO$_2$ | H | 2-OMe, 5-Cl | 81-85 | |
| 1-15 | Pr | H | — | H | 2-OMe | | |
| 1-16 | Pr | H | — | H | 2-Me | 93-97 | 120 |
| 1-17 | Pr | H | — | H | 2-Cl | | |
| 1-18 | Pr | H | — | H | 2-OMe, 5-Me | | |
| 1-19 | Pr | H | — | H | 2-OMe, 5-Cl | | |
| 1-20 | Pr | H | — | H | 2,3-(Me)$_2$ | | |
| 1-21 | Pr | H | — | H | 2-NO$_2$, 4-Cl | | |
| 1-22 | Pr | H | 2-NO$_2$ | H | 2-OMe, 5-Cl | | |
| 1-23 | Pr | H | 2-NO$_2$ | H | 2,3-(Me)$_2$ | 93-97 | |
| 1-24 | Pr | H | 2-NO$_2$ | H | 2-OMe | 93-97 | 197 |
| 1-25 | Pr | H | — | Me | 2-OMe, 5-Cl | | |
| 1-26 | Pr | H | — | Me | 2,3-(Me)$_2$ | 81-85 | |
| 1-27 | Pr | H | — | Me | 2-OMe, 5-Me | | |
| 1-28 | Pr | H | — | Me | 2-OMe | 93-97 | |
| 1-29 | Pr | H | 2-NO$_2$ | Me | 2-OMe, 5-Me | | |
| 1-30 | allyl | H | 2-NO$_2$ | H | 2-OMe | 81-85 | |
| 1-31 | allyl | H | — | Me | 2,5-(Me)$_2$ | | |
| 1-32 | allyl | H | — | Me | 2-OMe, 5-Me | 93-97 | |
| 1-33 | allyl | H | — | H | 2-NO$_2$, 4-Cl | | |
| 1-34 | allyl | Allyl | — | H | 2-OMe, 5-Me | | |
| 1-35 | allyl | Allyl | — | H | 2-Cl | | |
| 1-36 | allyl | Me | — | H | 2-Me | | |
| 1-37 | allyl | Me | — | H | 2-OMe | | |
| 1-38 | allyl | Me | — | H | 2-OMe, 5-Me | | |
| 1-39 | allyl | Me | — | H | 2-OMe, 5-Cl | 93-97 | 214 |
| 1-40 | Allyl | Me | — | H | 2,3-(Me)$_2$ | | |
| 1-41 | c-hexyl | H | — | H | 2-Cl | 93-97 | |
| 1-42 | c-hexyl | H | 2-NO$_2$ | H | 2-OMe, 5-Me | | |
| 1-43 | c-pentyl | H | 2-NO$_2$ | H | 2-OMe, 5-Me | | |
| 1-44 | c-pentyl | H | — | Me | 2-OMe, 5-Me | 93-97 | |
| 1-45 | c-Pr | H | — | H | 2-OMe | 96-100 | 217 |
| 1-46 | c-Pr | H | — | H | 2-Cl | 96-100 | 207 |
| 1-47 | c-Pr | H | — | H | 2-Me | 88-92 | 226 |
| 1-48 | c-Pr | H | — | H | 2-OMe, 5-Me | 88-92 | 211 |
| 1-49 | c-Pr | H | — | H | 2,3-(Me)$_2$ | 88-92 | 233 |
| 1-50 | c-Pr | H | — | H | 2,5-(Me)$_2$ | 93-97 | 225 |
| 1-51 | c-Pr | H | — | Me | 2-OMe | 88-92 | 70 |

TABLE 1-continued

Compounds of formula (Ia)

$$\text{R}^1\text{R}^2\text{N-C(O)-C}_6\text{H}_3(\text{R}^3)_n\text{-SO}_2\text{-N(R}^4)\text{-C(O)-C}_6\text{H}_4(\text{R}^5)_m \quad (Ia)$$

| Cpd No. | R¹ | R² | R³ | R⁴ | R⁵ | Yield % | Mp °C. |
|---|---|---|---|---|---|---|---|
| 1-52 | c-Pr | H | — | Me | 2-Me | 92-96 | 122 |
| 1-53 | c-Pr | H | — | Me | 2,5-(Me)$_2$ | 92-96 | |
| 1-54 | c-Pr | H | — | Me | 2-OMe, 5-Me | | |
| 1-55 | c-Pr | H | 2-NO$_2$ | H | 2-OMe, 5-Me | | |
| 1-56 | C$_2$H$_4$—OEt | H | — | H | 2-Cl | 92-96 | 138 |
| 1-57 | C$_2$H$_4$—OEt | H | — | H | 2-OMe | | |
| 1-58 | C$_2$H$_4$—OEt | H | — | H | 2-Me | 92-96 | 162 |
| 1-59 | C$_2$H$_4$—OEt | H | — | H | 2-OMe | | |
| 1-60 | C$_2$H$_4$—OEt | H | — | H | 2-Cl | 92-96 | 163 |
| 1-61 | C$_2$H$_4$—OEt | H | — | H | 2,5-(Me)$_2$ | | |
| 1-62 | C$_2$H$_4$—OEt | H | — | H | 2,5-Cl$_2$ | 92-96 | 185 |
| 1-63 | C$_2$H$_4$—OEt | H | — | H | 2,3-(Me)$_2$ | | |
| 1-64 | C$_2$H$_4$—OEt | H | — | H | 2-OMe, 5-Cl | 92-96 | 193 |
| 1-65 | C$_2$H$_4$—OEt | H | — | Me | 2,3-(Me)$_2$ | 92-96 | |
| 1-66 | C$_2$H$_4$—OEt | H | — | Me | 2-Me | 91-95 | |
| 1-67 | C$_2$H$_4$—OEt | H | — | Me | 2-OMe, 5-Me | | |
| 1-68 | C$_3$H$_6$—OMe | H | — | H | 2-Me | 92-96 | 93 |
| 1-69 | C$_3$H$_6$—OMe | H | — | H | 2-Cl | | |
| 1-70 | CH$_2$-2-furanyl | H | — | H | 2-Me | 92-96 | 205 |
| 1-71 | CH$_2$-2-furanyl | H | — | H | 2-OMe | 91-95 | 190 |
| 1-72 | CH$_2$-c-Pr | H | — | H | 2,5-Cl$_2$ | 91-95 | 209 |
| 1-73 | CH$_2$-c-Pr | H | — | H | 2,5-(Me)$_2$ | | |
| 1-74 | CH$_2$-c-Pr | H | — | H | 2-Me | | |
| 1-75 | CH$_2$-c-Pr | H | — | H | 2-OMe, 5-Me | | |
| 1-76 | CH$_2$-c-Pr | H | — | H | 2-OMe, 5-Cl | | |
| 1-77 | CH$_2$-c-Pr | H | — | H | 2-Cl | | |
| 1-78 | CH$_2$C≡CH | H | — | H | 2,5-Cl$_2$ | 92-96 | 175 |
| 1-79 | CH$_2$C≡CH | H | — | Me | 2,5-(Me)$_2$ | 88-92 | 185 |
| 1-80 | CH$_2$C≡CH | CH$_2$C≡CH | — | Me | 2-OMe, 5-Me | 88-92 | |
| 1-81 | CH$_2$-t-Bu | H | — | H | 2-Cl | 88-92 | 213 |
| 1-82 | CH$_2$-t-Bu | H | — | H | 2-OMe | | |
| 1-83 | CH$_2$-t-Bu | H | — | H | 2-Me | | |
| 1-84 | CH$_2$CH(OMe)$_2$ | H | — | H | 2-OMe | | |
| 1-85 | CH$_2$CH(OMe)$_2$ | H | — | H | 2-Me | 88-92 | 140 |
| 1-86 | Et | Et | — | H | 2-OMe | | |
| 1-87 | Et | Et | — | H | 2-Cl | | |
| 1-88 | Et | Et | — | H | 2,5-Cl$_2$ | 88-92 | 155 |
| 1-89 | Et | Et | — | H | 2-OMe | 88-92 | |
| 1-90 | Et | H | — | H | 2,5-(Me)$_2$ | | |
| 1-91 | Et | H | — | H | 2,3-(Me)$_2$ | 88-92 | |
| 1-92 | Et | H | — | Me | 2-OMe | | |
| 1-93 | Et | H | — | Me | 2-OMe, 5-Me | | |
| 1-94 | Et | H | 2-NO$_2$ | H | 2-OMe, 5-Me | 88-92 | |
| 1-95 | i-Bu | H | — | H | 2-OMe | | |
| 1-96 | i-Bu | H | — | H | 2-Me | 88-92 | 150 |
| 1-97 | i-Bu | H | — | H | 2-Cl | | |
| 1-98 | i-Bu | H | — | H | 2,3-(Me)$_2$ | | |
| 1-99 | i-Bu | H | — | H | 2-OMe, 5-Me | | |
| 1-100 | i-Bu | H | — | H | 2,5-(Me)$_2$ | | |
| 1-101 | i-Pr | H | — | H | 2-Me | 88-92 | 200 |
| 1-102 | i-Pr | H | — | H | 2-OMe | | |
| 1-103 | i-Pr | H | — | H | 2-Cl | | |
| 1-104 | i-Pr | H | — | H | 2,4-Cl$_2$ | 88-92 | 258 |
| 1-105 | i-Pr | H | — | H | 2,5-Cl$_2$ | | |
| 1-106 | i-Pr | H | — | Me | 2-OMe, 5-Me | | |
| 1-107 | i-Pr | H | — | Me | 2,5-(Me)$_2$ | | |
| 1-108 | i-Pr | H | — | H | 2-NO$_2$, 4-Cl | | |
| 1-109 | i-Pr | H | 2-NO$_2$ | H | 2-Me | | |
| 1-110 | i-Pr | H | 2-NO$_2$ | H | 2-OMe, 5-Me | | |
| 1-111 | i-Pr | H | 2-NO$_2$ | H | 2,5-(Me)$_2$ | | |
| 1-112 | Me | H | — | H | 2,3-(Me)$_2$ | 88-92 | 227 |
| 1-113 | Me | H | — | H | 2,5-Cl$_2$ | | |
| 1-114 | Me | H | — | H | 2-Me | | |
| 1-115 | Me | H | — | H | 2-OMe, 5-Me | | |
| 1-116 | Me | H | — | H | 2,5-(Me)$_2$ | | |
| 1-117 | Me | H | — | H | 2-NO$_2$, 4-Cl | 88-92 | |

TABLE 1-continued

Compounds of formula (Ia)

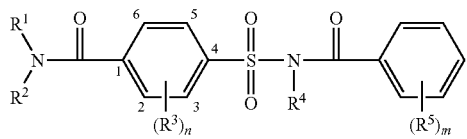

(Ia)

| Cpd No. | $R^1$ | $R^2$ | $R^3$ | $R^4$ | $R^5$ | Yield % | Mp °C. |
|---|---|---|---|---|---|---|---|
| 1-118 | Me | H | — | H | 2-Cl | | |
| 1-119 | Me | H | 2-$NO_2$ | H | 2-OMe, 5-Me | | |
| 1-120 | Me | H | — | Me | 2,5-$(Me)_2$ | | |
| 1-121 | Me | Et | — | H | 2-Cl | 88-92 | 188 |
| 1-122 | Me | Et | — | H | 2-OMe | | |
| 1-123 | Me | Et | — | H | 2-Me | | |
| 1-124 | Me | Et | — | H | 2-$NO_2$, 4-Cl | 88-92 | |
| 1-125 | Me | Et | — | H | 2-OMe, 5-Me | | |
| 1-126 | Me | Et | 2-$NO_2$ | H | 2-OMe, 5-Me | | |
| 1-127 | Me | Et | — | Me | 2,5-$(Me)_2$ | | |
| 1-128 | Me | Me | — | H | 2-OMe | | |
| 1-129 | Me | Me | — | H | 2-Me | | |
| 1-130 | Me | Me | — | H | 2-Cl | | |
| 1-131 | Me | Me | — | H | 2-OMe, 5-Me | | |
| 1-132 | Me | Me | — | H | 2,5-$(Me)_2$ | | |
| 1-133 | Me | Me | — | H | 2,3-$(Me)_2$ | 88-92 | 205 |
| 1-134 | Me | Allyl | — | H | 2-Cl | | |
| 1-135 | —$(CH_2)_2$—O—$(CH_2)_2$— | | — | H | 2-OMe | | |
| 1-136 | —$(CH_2)_2$—O—$(CH_2)_2$— | | — | H | 2-OMe, 5-Me | | |
| 1-137 | —$(CH_2)_2$—O—$(CH_2)_2$— | | — | H | 2-Cl | | |
| 1-138 | —$(CH_2)_4$— | | — | H | 2-$NO_2$, 4-Cl | | |
| 1-139 | —$(CH_2)_5$— | | — | H | 2,5-$(Me)_2$ | 88-92 | 157 |
| 1-140 | —$(CH_2)_5$— | | — | H | 2,5-$Cl_2$ | | |
| 1-141 | —$(CH_2)_5$— | | — | H | 2-OMe, 5-Cl | | |
| 1-142 | —$(CH_2)_5$— | | — | H | 2-$NO_2$, 4-Cl | | |
| 1-143 | —$C_2H_4$—$C_6H_5$ | H | — | H | 2-OMe, 5-Me | | |
| 1-144 | —$C_2H_4$—$C_6H_5$ | H | — | H | 2-OMe, 5-Cl | | |
| 1-145 | —$C_2H_4$—$C_6H_5$ | H | — | H | 2-OMe | | |
| 1-146 | —$(CH_2)_4$— | | — | Me | 2-OMe, 5-Cl | | |
| 1-147 | Me | Et | — | Me | 2-OMe | | |
| 1-148 | Pr | Pr | — | H | 2-OMe, 5-Cl | | |
| 1-149 | Pr | Pr | — | H | 2,5-$(Me)_2$ | | |
| 1-150 | Et | H | — | H | 2-OMe | | |
| 1-151 | Et | H | — | H | 2-OMe, 5-Cl | | |
| 1-152 | $CH_2C\equiv CH$ | $CH_2C\equiv CH$ | — | H | 2-OMe, 5-Cl | | |
| 1-153 | $CH(CH_3)$—$C_3H_7$ | H | — | H | 2-OMe, 5-Cl | | |
| 1-154 | c-Pr | H | — | H | 2-O—$CH_2CH_2$-3 | | |
| 1-155 | s-Bu | H | — | H | 2-OMe, 5-Cl | | |
| 1-156 | s-Bu | H | — | H | 2-OMe | | |
| 1-157 | 2-heptyl | H | — | H | 2-OMe, 5-Cl | | |
| 1-158 | 2-heptyl | H | — | H | 2-OMe | | |
| 1-159 | Me | Me | — | H | 2-OMe, 5-Cl | | |
| 1-160 | Me | Et | — | Me | 2-Me | | |
| 1-161 | c-Pr | H | 2-$NO_2$ | H | 2-OMe | | |
| 1-162 | Pr | H | 2-Cl | H | 2-Me | | |
| 1-163 | c-Pr | H | 2-Cl | H | 2-OMe | | |

TABLE 2

Compounds of formula (Ib)

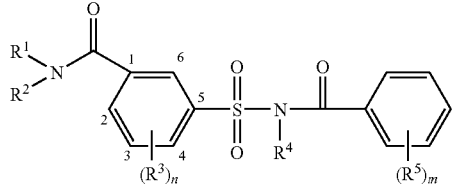

| Cpd No. | R¹ | R² | R³ | R⁴ | R⁵ | Yield % | Mp °C. |
|---|---|---|---|---|---|---|---|
| 2-1 | Pr | H | 2,4-Cl₂ | H | 2,5-(Me)₂ | | |
| 2-2 | Pr | H | 2,4-Cl₂ | H | 2-OMe | | |
| 2-3 | Pr | H | 2,4-Cl₂ | H | 2-Cl | | |
| 2-4 | Pr | H | 2,4-Cl₂ | H | 2-Me | 86-90 | |
| 2-5 | Pr | H | 2,4-Cl₂ | H | 2,3-(Me)₂ | 85-89 | |
| 2-6 | Pr | H | 2,4-Cl₂ | H | 2-OMe, 5-Me | 84-88 | |
| 2-7 | Pr | H | 2,4-Cl₂ | H | 2-NO₂, 4-Cl | 84-88 | |
| 2-8 | Pr | H | 2,4-Cl₂ | Me | 2-OMe, 5-Me | 83-87 | |
| 2-9 | Pr | H | H | H | 2-OMe, 5-Me | | |
| 2-10 | Pr | H | H | H | 2-OMe, 5-Cl | 76-80 | |
| 2-11 | Pr | H | H | H | 2-OMe | | |
| 2-12 | Pr | H | H | H | 2,5-(Me)₂ | 76-80 | |
| 2-13 | Bu | H | 2,4-Cl₂ | H | 2,5-(Me)₂ | | |
| 2-14 | Bu | H | 2,4-Cl₂ | H | 2-OMe, 5-Me | | |
| 2-15 | Bu | H | 2,4-Cl₂ | H | 2-OMe, 5-Cl | | |
| 2-16 | Bu | H | H | H | 2-OMe, 5-Me | | |
| 2-17 | Bu | H | H | H | 2-OMe, 5-Cl | | |
| 2-18 | Bu | H | H | H | 2-OMe | | |
| 2-19 | Bu | H | H | H | 2,5-(Me)₂ | | |
| 2-20 | Me | H | 4-Cl | H | 2-Cl | | |
| 2-21 | Me | H | 4-Cl | H | 2-Me | | |
| 2-22 | Me | H | 4-Cl | H | 2,3-(Me)₂ | 87-91 | 215 |
| 2-23 | Me | Me | 2,4-Cl₂ | H | 2-OMe, 5-Me | | |
| 2-24 | Me | Me | 2,4-Cl₂ | H | 2-OMe, 5-Cl | | |
| 2-25 | Me | Me | 2,4-Cl₂ | H | 2-NO₂, 4-Cl | | |
| 2-26 | Me | Me | 4-Cl | H | 2-OMe, 5-Me | | |
| 2-27 | Me | Me | 4-Cl | H | 2-OMe, 5-Cl | | |
| 2-28 | Me | Me | 4-Cl | H | 2-NO₂, 4-Cl | 87-91 | |
| 2-29 | Me | Me | 4-Cl | Me | 2-OMe, 5-Me | | |
| 2-30 | Me | Me | H | H | 2-OMe, 5-Me | | |
| 2-31 | Me | Me | H | H | 2-NO₂, 4-Cl | | |
| 2-32 | Me | Me | H | H | 2-OMe | | |
| 2-33 | C₂H₄—OMe | H | 2,4-Cl₂ | H | 2-OMe | | |
| 2-34 | C₂H₄—OMe | H | 2,4-Cl₂ | H | 2-Me | | |
| 2-35 | C₂H₄—OMe | H | 2,4-Cl₂ | H | 2,5-(Me)₂ | | |
| 2-36 | C₂H₄—OMe | H | 2,4-Cl₂ | H | 2-Cl | | |
| 2-37 | C₂H₄—OMe | H | 2,4-Cl₂ | H | 2,5-Cl₂ | | |
| 2-38 | c-Pr | H | 2,4-Cl₂ | H | 2,5-(Me)₂ | | |
| 2-39 | c-Pr | H | 2,4-Cl₂ | H | 2-OMe | 84-88 | 174 |
| 2-40 | c-Pr | H | 2,4-Cl₂ | H | 2-Cl | | |
| 2-41 | c-Pr | H | 2,4-Cl₂ | H | 2-Me | | |
| 2-42 | c-Pr | H | 4-Cl | H | 2-OMe | | |
| 2-43 | c-Pr | H | 4-Cl | H | 2-Me | | |
| 2-44 | c-Pr | H | 2,4-Cl₂ | H | 2,5-Cl₂ | | |
| 2-45 | c-Pr | H | 2,4-Cl₂ | H | 2,3-(Me)₂ | 83-87 | |
| 2-46 | c-Pr | H | 2,4-Cl₂ | H | 2-OMe, 5-Me | | |
| 2-47 | c-Pr | H | 2,4-Cl₂ | H | 2-OMe, 5-Cl | | |
| 2-48 | c-Pr | H | 2,4-Cl₂ | H | 2-NO₂, 4-Cl | | |
| 2-49 | c-Pr | H | 4-Cl | H | 2-Cl | | |
| 2-50 | c-Pr | H | 4-Cl | H | 2,5-(Me)₂ | | |
| 2-51 | c-Pr | H | 4-Cl | H | 2-OMe, 5-Me | 83-87 | |
| 2-52 | c-Pr | H | 4-Cl | H | 2-OMe, 5-Cl | | |
| 2-53 | c-Pr | H | 4-Cl | H | 2-NO₂, 4-Cl | | |
| 2-54 | c-Pr | H | 4-Cl | Me | 2-OMe, 5-Me | | |
| 2-55 | c-Pr | H | H | H | 2,5-(Me)₂ | | |
| 2-56 | c-Pr | H | H | H | 2-OMe, 5-Me | 76-80 | |
| 2-57 | c-Pr | H | H | H | 2-OMe, 5-Cl | | |
| 2-58 | c-Pr | H | H | H | 2-NO₂, 4-Cl | | |
| 2-59 | allyl | H | 2,4-Cl₂ | H | 2-OMe | | |
| 2-60 | allyl | H | 2,4-Cl₂ | H | 2-Cl | | |
| 2-61 | CH₂C≡CH | H | 2,4-Cl₂ | H | 2,5-(Me)₂ | | |
| 2-62 | CH₂C≡CH | H | 2,4-Cl₂ | H | 2-OMe, 5-Me | | |
| 2-63 | CH₂C≡CH | H | 2,4-Cl₂ | H | 2-OMe, 5-Cl | | |
| 2-64 | CH₂C≡CH | H | 2,4-Cl₂ | H | 2-NO₂, 4-Cl | | |
| 2-65 | CH₂C≡CH | H | 2,4-Cl₂ | Me | 2-OMe, 5-Me | | |
| 2-66 | CH₂C≡CH | H | 4-Cl | H | 2,5-(Me)₂ | | |
| 2-67 | CH₂C≡CH | H | 4-Cl | H | 2-OMe, 5-Me | | |
| 2-68 | CH₂C≡CH | H | 4-Cl | H | 2-OMe, 5-Cl | | |
| 2-69 | CH₂C≡CH | H | 4-Cl | H | 2-NO₂, 4-Cl | | |
| 2-70 | —(CH₂)₄— | | 2,4-Cl₂ | H | 2,5-(Me)₂ | | |
| 2-71 | —(CH₂)₄— | | 2,4-Cl₂ | H | 2-OMe, 5-Me | | |
| 2-72 | —(CH₂)₄— | | 2,4-Cl₂ | H | 2-OMe, 5-Cl | | |
| 2-73 | —(CH₂)₄— | | 2,4-Cl₂ | H | 2-NO₂, 4-Cl | | |
| 2-74 | —(CH₂)₄— | | H | H | 2-OMe, 5-Me | | |
| 2-75 | —(CH₂)₄— | | H | H | 2-OMe | | |
| 2-76 | Me | Et | H | H | 2-OMe, 5-Cl | | |
| 2-77 | Me | Et | H | H | 2-OMe | | |
| 2-78 | i-Pr | H | H | H | 2,5-(Me)₂ | | |
| 2-79 | Me | H | H | H | 2-OMe | | |
| 2-80 | Me | H | H | H | 2,5-(Me)₂ | | |

TABLE 3

Compounds of formula (Ic)

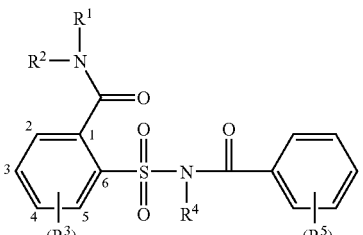

| Cpd No. | R¹ | R² | R³ | R⁴ | R⁵ | Yield % | Mp °C. |
|---|---|---|---|---|---|---|---|
| 3-1 | Pr | H | H | H | 2,5-(Me)₂ | | |
| 3-2 | Pr | H | H | H | 2-OMe | | |
| 3-3 | Pr | H | H | H | 2-Cl | | |
| 3-4 | Pr | H | H | H | 2-Me | | |
| 3-5 | Pr | H | H | H | 2,3-(Me)₂ | | |
| 3-6 | Pr | H | H | H | 2-OMe, 5-Me | | |
| 3-7 | Pr | H | H | H | 2-OMe, 5-Cl | | |
| 3-8 | Pr | H | H | H | 2-NO₂, 4-Cl | | |
| 3-9 | Pr | H | H | Me | 2-OMe, 5-Me | | |
| 3-10 | Pr | H | 2-Cl | H | 2-OMe, 5-Me | | |
| 3-11 | Pr | H | 2-Cl | H | 2,5-(Me)₂ | | |
| 3-12 | Bu | H | H | H | 2,5-(Me)₂ | | |
| 3-13 | Bu | H | H | H | 2-OMe, 5-Me | | |
| 3-14 | Bu | H | H | H | 2-OMe, 5-Cl | | |
| 3-15 | Bu | H | H | H | 2-NO₂, 4-Cl | | |
| 3-16 | Bu | H | 2-Cl | H | 2-OMe, 5-Me | | |
| 3-17 | Bu | H | 2-Cl | H | 2-OMe, 5-Cl | | |
| 3-18 | Bu | H | 2-Cl | H | 2-OMe | | |
| 3-19 | Bu | H | 2-Cl | H | 2,5-(Me)₂ | | |
| 3-20 | Me | H | 2-Cl | H | 2-Cl | | |
| 3-21 | Me | H | 2-Cl | H | 2-Me | | |
| 3-22 | Me | H | 2-Cl | H | 2,3-(Me)₂ | | |
| 3-23 | Me | Me | H | H | 2-OMe, 5-Me | | |
| 3-24 | Me | Me | H | H | 2-OMe, 5-Cl | | |

TABLE 3-continued

Compounds of formula (Ic)

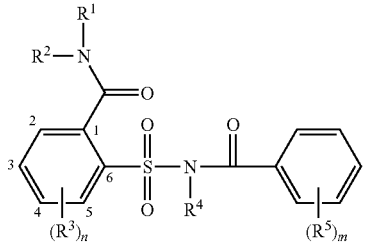

(Ic)

| Cpd No. | R¹ | R² | R³ | R⁴ | R⁵ | Yield % | Mp °C. |
|---|---|---|---|---|---|---|---|
| 3-25 | Me | Me | H | H | 2-NO₂, 4-Cl | | |
| 3-26 | Me | Me | 2-Cl | H | 2-OMe, 5-Me | | |
| 3-27 | Me | Me | 2-Cl | H | 2-OMe, 5-Cl | | |
| 3-28 | Me | Me | 2-Cl | H | 2-NO₂, 4-Cl | | |
| 3-29 | Me | Me | 2-Cl | Me | 2-OMe, 5-Me | | |
| 3-30 | Me | Me | 4-NO₂ | H | 2-OMe, 5-Me | | |
| 3-31 | Me | Me | 4-NO₂ | H | 2-OMe | | |
| 3-32 | C₂H₄—OMe | H | H | H | 2-OMe | | |
| 3-33 | C₂H₄—OMe | H | H | H | 2,5-Cl₂ | | |
| 3-34 | c-Pr | H | H | H | 2,5-(Me)₂ | | |
| 3-35 | c-Pr | H | H | H | 2-OMe | | |
| 3-36 | c-Pr | H | H | H | 2-Cl | | |
| 3-37 | c-Pr | H | H | H | 2-Me | | |
| 3-38 | c-Pr | H | 2-Cl | H | 2-OMe | | |
| 3-39 | c-Pr | H | 2-Cl | H | 2-Me | | |
| 3-40 | c-Pr | H | 2-Cl | H | 2-Cl | | |
| 3-41 | c-Pr | H | 2-Cl | H | 2,5-(Me)₂ | | |
| 3-42 | c-Pr | H | 2-Cl | H | 2-OMe, 5-Me | | |
| 3-43 | c-Pr | H | 2-Cl | H | 2-NO₂, 4-Cl | | |
| 3-44 | c-Pr | H | 2-Cl | Me | 2-OMe, 5-Me | | |
| 3-45 | allyl | H | H | H | 2-OMe | | |
| 3-46 | allyl | H | H | H | 2-Cl | | |
| 3-47 | allyl | H | H | H | 2,5-(Me)₂ | | |
| 3-48 | allyl | H | H | H | 2,5-Cl₂ | | |
| 3-49 | CH₂C≡CH | H | H | H | 2,5-(Me)₂ | | |
| 3-50 | CH₂C≡CH | H | H | H | 2-OMe, 5-Me | | |

Tables 4 to 6 list some examples of compounds of formula (IV) which are prepared:

TABLE 4

Compounds of formula (IVa)

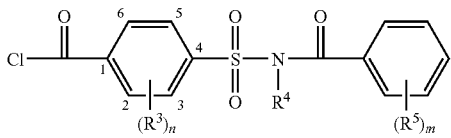

(IVa)

| Cpd No. | R³ | R⁴ | R⁵ | Yield % | Mp °C. |
|---|---|---|---|---|---|
| 4-1 | — | H | — | 94-98 | 182 |
| 4-2 | — | H | 2,3-(Me)₂ | 90-94 | |
| 4-3 | — | H | 2,4-Cl₂ | 94-98 | |
| 4-4 | — | H | 2,5-Cl₂ | 90-94 | 140 |
| 4-5 | — | H | 2,5-(Me)₂ | 89-93 | |
| 4-6 | — | H | 2-Cl | 93-97 | 198 |
| 4-7 | — | H | 2-Me | 92-96 | |
| 4-8 | — | H | 2-NO₂, 4-Cl | 90-94 | 178 |
| 4-10 | — | H | 2-OMe | 92-96 | 126 |
| 4-11 | — | H | 2-OMe, 5-Cl | 91-95 | 138-140 |
| 4-12 | 2-Cl | H | 2-OMe, 5-Me | 88-92 | 160-163 |
| 4-13 | 3-Cl | H | 2-OMe, 5-Cl | 90-94 | 165 |
| 4-14 | — | Me | 2,3-(Me)₂ | 93-97 | |
| 4-15 | — | Me | 2,5-(Me)₂ | 88-92 | |
| 4-17 | — | Me | 2-Me | 93-97 | |
| 4-18 | — | Me | 2-OMe | 88-92 | |
| 4-19 | — | Me | 2-OMe, 5-Cl | 93-97 | |
| 4-20 | — | Me | 2-OMe, 5-Me | 88-92 | |
| 4-21 | 2-Cl | H | 2-Me | 93-97 | |
| 4-22 | 2-Cl | H | 2-OMe | 88-92 | 128 |
| 4-23 | 2-Cl | H | 2-OMe, 5-Cl | 90-94 | |
| 4-24 | 2-NO₂ | H | 2,3-(Me)₂ | 93-97 | |
| 4-25 | 2-NO₂ | H | 2,5-(Me)₂ | 93-97 | |
| 4-26 | 2-NO₂ | H | 2-Cl | 88-92 | |
| 4-27 | 2-NO₂ | H | 2-Me | 93-97 | 130 |
| 4-28 | 2-NO₂ | H | 2-OMe | 90-94 | 123 |
| 4-29 | 2-NO₂ | H | 2-OMe, 5-Cl | 88-92 | 112 |
| 4-30 | 2-NO₂ | H | 2-OMe, 5-Me | 90-94 | 125 |
| 4-31 | 2-NO₂ | H | 2-OMe, 5-Me | 88-92 | 139 |

TABLE 5

Compounds of formula (IVb)

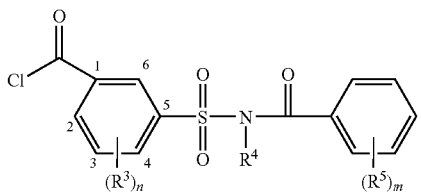

(IVb)

| Cpd No. | R³ | R⁴ | R⁵ | Yield % | Mp °C. |
|---|---|---|---|---|---|
| 5-1 | 2,4-Cl2 | H | 2-NO₂, 4-Cl | | |
| 5-2 | 2,4-Cl2 | H | 2,3-(Me)₂ | 86-90 | |
| 5-3 | 2,4-Cl2 | H | 2,5-(Me)₂ | | |
| 5-4 | 2,4-Cl2 | H | 2-Cl | 76-80 | |
| 5-5 | 2,4-Cl2 | H | 2-NO₂, 4-Cl | | |
| 5-7 | 2,4-Cl2 | H | 2-OMe | 87-91 | |
| 5-8 | 2,4-Cl2 | H | 2-OMe, 5-Cl | 82-86 | |
| 5-9 | 2,4-Cl2 | H | 2-OMe, 5-Me | 77-81 | |
| 5-10 | 2,4-Cl2 | Me | 2-OMe, 5-Me | | |
| 5-11 | 2,4-Cl2 | H | 2,3-(Me)₂ | 75-79 | |
| 5-15 | 2,4-Cl2 | H | 2-Me | | |
| 5-16 | 2,4-Cl2 | H | 2-NO₂, 4-Cl | | |
| 5-17 | 2,4-Cl2 | H | 2-OMe | | |
| 5-18 | 2,4-Cl2 | H | 2-OMe, 5-Cl | 82-86 | |
| 5-19 | 2,4-Cl2 | H | 2-OMe, 5-Me | | |
| 5-20 | 2,4-Cl2 | Me | 2-OMe, 5-Me | | |
| 5-21 | 4-Cl | H | 2,3-(Me)₂ | 82-86 | |
| 5-22 | 4-Cl | H | 2,5-(Me)₂ | | |
| 5-23 | 4-Cl | H | 2-Cl | 74-78 | |
| 5-24 | 4-Cl | H | 2-Me | | |
| 5-25 | 4-Cl | H | 2-NO₂, 4-Cl | | |
| 5-26 | 4-Cl | H | 2-OMe | 76-80 | |
| 5-27 | 4-Cl | H | 2-OMe, 5-Cl | | |
| 5-29 | 4-Cl | Me | 2-OMe, 5-Me | 82-86 | |
| 5-31 | — | H | 2-NO₂, 4-Cl | | |
| 5-32 | — | H | 2-OMe | 81-85 | |
| 5-33 | — | H | 2-OMe, 5-Cl | | |
| 5-34 | — | H | 2-OMe, 5-Me | 82-86 | |

TABLE 6

Compounds of formula (IVc)

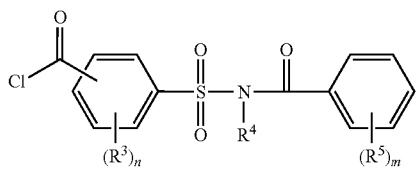

(IVc)

| Cpd No. | R³ | R⁴ | R⁵ | Yield % | Mp °C. |
|---|---|---|---|---|---|
| 6-1 | 2-Cl | H | 2,3-(Me)₂ | 81-85 | 180-185 |
| 6-2 | 2-Cl | H | 2,5-(Me)₂ | 93-97 | 102 |
| 6-3 | 2-Cl | H | 2-Cl | 92-96 | 110 |
| 6-4 | 2-Cl | H | 2-Me | 88-92 | |
| 6-6 | 2-Cl | H | 2-OMe | 93-97 | 118 |
| 6-7 | 2-Cl | H | 2-OMe, 5-Cl | 91-95 | |
| 6-8 | 2-Cl | H | 2-OMe, 5-Me | 87-91 | |
| 6-9 | 2-Cl | Me | 2-OMe, 5-Me | 87-91 | 98 |
| 6-10 | 4-NO₂ | H | 2-NO₂, 4-Cl | 89-93 | |
| 6-13 | 4-NO₂ | H | 2-OMe, 5-Me | 90-94 | |
| 6-16 | — | H | 2,5-Cl₂ | 89-93 | |
| 6-17 | — | H | 2-Cl | 92-96 | |
| 6-18 | — | H | 2-Me | 91-95 | |
| 6-19 | — | H | 2-NO₂, 4-Cl | 88-92 | |
| 6-20 | — | H | 2-OMe | 88-92 | |
| 6-21 | — | H | 2-OMe, 5-Cl | 88-92 | |
| 6-22 | — | H | 2-OMe, 5-Me | 88-92 | |
| 6-23 | — | Me | 2-OMe, 5-Me | 88-92 | |

The invention claimed is:

1. A compound of formula (IV):

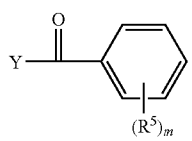

(IV)

in which R³ and R⁵ are each independently halogen, ($C_1$-$C_6$)-alkyl, ($C_1$-$C_6$)-haloalkyl, ($C_1$-$C_6$)-alkoxy, $S(O)_q$—($C_1$-$C_6$)-alkyl, ($C_1$-$C_6$)-alkylcarbonyl, —CO-aryl, cyano or nitro; or two adjacent R⁵ groups form a —O—$CH_2CH_2$— moiety, R⁴ is hydrogen, ($C_1$-$C_4$)-alkyl, ($C_2$-$C_4$)-alkenyl or ($C_2$-$C_4$)-alkynyl, n is an integer from 0 to 4, m is an integer from 0 to 5, and q is 0, 1 or 2; or a salt thereof.

2. A compound or a salt thereof as claimed in claim 1, wherein
R³ is each independently halogen, ($C_1$-$C_4$)-alkyl, ($C_1$-$C_4$)-haloalkyl, ($C_1$-$C_4$)-alkoxy, $S(O)_q$—($C_1$-$C_4$)-alkyl, cyano or nitro,
R⁴ is hydrogen or ($C_1$-$C_4$)-alkyl,
R⁵ is each independently halogen, ($C_1$-$C_4$)-alkyl, ($C_1$-$C_4$)-haloalkyl, ($C_1$-$C_4$)-alkoxy, cyano or nitro,
n is 0, 1 or 2,
m is 0 or 1 or 2, and
q is 0, 1 or 2.

3. A compound or a salt thereof as claimed in claim 1, wherein
R⁴ is hydrogen,
R³ is ($C_1$-$C_6$)-alkoxy,
n is 0,
m is 0 or 1,
and the sulfamoyl group is located para to the COCl moiety in the phenyl ring.

4. A compound or a salt thereof as claimed in claim 1, wherein
R⁴ is hydrogen,
R⁵ is ($C_1$-$C_4$)-alkoxy,
n is 0,
m is 1,
and the sulfamoyl group is located para to the COCl moiety in the phenyl ring.

5. A process for the preparation of a compound of formula (IV), or a salt thereof, as defined in claim 1, which comprises reaction of a compound of formula (II):

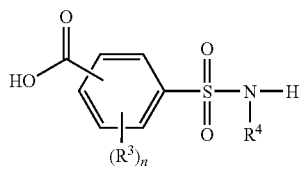

(II)

wherein R³, R⁴ and n are as defined in formula (IV),
with a compound of formula (III):

(III)

wherein R⁵ and m are as defined in formula (IV) and Y is OH or Cl, in the presence of a chlorinating agent.

6. A process as claimed in claim 5 wherein Y is OH.

7. A process as claimed in claim 5 wherein the chlorinating agent is thionylchloride.

8. A process as claimed in claim 5 wherein the amount of chlorinating agent used is, when Y is OH from 1 to 2 molar equivalents per equivalents of (II) and (IIIa), or when Y is Cl from 1 to 2 molar equivalents per equivalent of (II).

9. A process as claimed in claim 5, wherein the solvent used in the reaction of the compound of formula (II) with the compound of formula (III) is chlorobenzene.

10. A process for the preparation of a compound of formula (I) or a salt thereof,

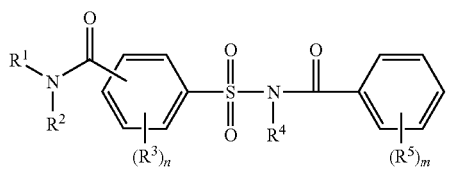

(I)

wherein:
R¹ is hydrogen, —$(CH_2)_p$-heterocyclyl or a hydrocarbon radical, where the two last-mentioned radicals are unsubstituted or substituted by one or more radicals selected from the group consisting of halogen, ($C_1$-$C_6$)-alkyl, ($C_1$-$C_6$)-haloalkyl, ($C_1$-$C_6$)-alkoxy, cyano and nitro;

$R^2$ is hydrogen, $(C_1-C_6)$-alkyl, $(C_2-C_6)$-alkenyl, $(C_2-C_6)$-alkynyl, $(C_1-C_6)$-alkoxy, $(C_2-C_6)$-alkenyloxy, where the five last-mentioned radicals are unsubstituted or substituted by one or more radicals selected from the group consisting of halogen, $(C_1-C_4)$-alkoxy and $(C_1-C_4)$-alkylthio; or $R^1$ and $R^2$ together with the linking nitrogen atom form a 3- to 8-membered saturated or unsaturated ring;

$R^3$ and $R^5$ are each independently halogen, $(C_1-C_6)$-alkyl, $(C_1-C_6)$-haloalkyl, $(C_1-C_6)$-alkoxy, $S(O)_q$—$(C_1-C_6)$-alkyl, $(C_1-C_6)$-alkylcarbonyl, —CO-aryl, cyano or nitro; or two adjacent $R^5$ groups form a —O—$CH_2CH_2$— moiety;

$R^4$ is hydrogen, $(C_1-C_4)$-alkyl, $(C_2-C_4)$-alkenyl or $(C_2-C_4)$-alkynyl;

n is an integer from 0 to 4;

m is an integer from 0 to 5;

p is 0 or 1; and q is 0, 1 or 2; or a salt thereof, which process comprises the reaction of a compound of formula (IV),

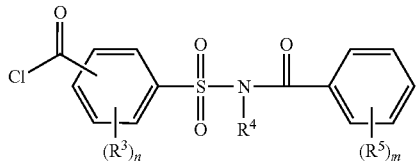

(IV)

in which $R^3$, $R^4$, $R^5$ m and n are defined as in formula (I), with a compound of formula (V):

$R^1R^2NH$ (V)

wherein $R^1$, $R^2$, $R^3$, $R^4$, $R^5$, m and n are as defined in formula (I), in the presence of a base.

11. A process as claimed in claim 10, wherein
$R^3$ is each independently halogen, $(C_1-C_4)$-alkyl, $(C_1-C_4)$-haloalkyl, $(C_1-C_4)$-alkoxy, $S(O)_q$—$(C_1-C_4)$-alkyl, cyano or nitro,
$R^4$ is hydrogen or $(C_1-C_4)$-alkyl,
$R^5$ is each independently halogen, $(C_1-C_4)$-alkyl, $(C_1-C_4)$-haloalkyl, $(C_1-C_4)$-alkoxy, cyano or nitro,
n is 0, 1 or 2,
m is 0 or 1 or 2, and
q is 0, 1 or 2.

12. A process as claimed in claim 10, wherein
$R^4$ is hydrogen,
$R^5$ is $(C_1-C_6)$-alkoxy,
n is 0,
m is 0 or 1,
and the sulfamoyl group is located para to the COCl moiety in the phenyl ring.

13. A compound or a salt thereof as claimed in claim 1, wherein $R^3$ is $(C_5-C_6)$-haloalkyl, $S(O)_q$—$(C_1-C_6)$-alkyl, $(C_5-C_6)$-alkylcarbonyl, —CO-aryl; or two adjacent $R^5$ groups form a —O—$CH_2CH_2$— moiety.

14. A compound or a salt thereof as claimed in claim 1, wherein $R^5$ is $(C_5-C_6)$-haloalkyl, $S(O)_q$—$(C_1-C_6)$-alkyl, $(C_5-C_6)$-alkylcarbonyl, —CO-aryl; or two adjacent $R^5$ groups form a —O—$CH_2CH_2$— moiety.

15. A compound or a salt thereof as claimed in claim 1, wherein $R^3$ and $R^5$ are each independently $(C_5-C_6)$-haloalkyl, $S(O)_q$—$(C_1-C_6)$-alkyl, $(C_5-C_6)$-alkylcarbonyl, —CO-aryl; or two adjacent $R^5$ groups form a —O—$CH_2CH_2$— moiety.

* * * * *